(12) United States Patent
Rosenman et al.

(10) Patent No.: US 6,322,526 B1
(45) Date of Patent: *Nov. 27, 2001

(54) VALVE SIZER

(76) Inventors: Daniel C. Rosenman, 216 Grand Blvd. #2, San Mateo, CA (US) 94401; Michi E. Garrison, 2325 Casa Bona Ave., Belmont, CA (US) 94002; Sean Christopher Daniel, One St. Francis Pl., San Franciso, CA (US) 94107

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,453

(22) Filed: Feb. 25, 2000

Related U.S. Application Data (60) Continuation of application No. 09/273,955, filed on Mar. 22, 1999, now Pat. No. 6,042,554, which is a division of application No. 08/646,850, filed on May 8, 1996, now Pat. No. 5,885,228.

(51) Int. Cl.$^7$ ........................................................ A61B 5/00
(52) U.S. Cl. .................................. 600/587; 623/2; 623/900
(58) Field of Search ............................. 600/587, 590, 600/591; 623/2, 900; 604/104; 606/194; 33/511, 512

(56) References Cited

U.S. PATENT DOCUMENTS

| | | | |
|---|---|---|---|
| 4,016,867 | * 4/1977 | King et al. | 128/25 |
| 4,056,854 | * 11/1977 | Boretos et al. | 3/1.5 |
| 4,211,241 | * 7/1980 | Kaster et al. | 128/774 |
| 4,362,167 | * 12/1982 | Nicolai et al. | 128/778 |
| 4,566,465 | * 1/1986 | Arhan et al. | 128/778 |
| 4,585,453 | * 4/1986 | Martin et al. | 623/2 |
| 4,602,911 | * 7/1986 | Ahmadi et al. | 623/2 |
| 4,679,556 | * 7/1987 | Lubock et al. | 128/303 R |
| 4,685,474 | * 8/1987 | Kurz et al. | 128/778 |
| 5,010,892 | * 4/1991 | Colvin et al. | 128/774 |
| 5,042,161 | * 8/1991 | Hodge | 33/501.45 |
| 5,053,008 | * 10/1991 | Bajaj | 604/104 |
| 5,089,015 | * 2/1992 | Ross | 623/2 |
| 5,171,248 | * 12/1992 | Ellis | 606/102 |
| 5,236,450 | * 8/1993 | Scott | 623/2 |
| 5,360,014 | * 11/1994 | Sauter et al. | 128/774 |
| 5,471,756 | * 12/1995 | Bolanos et al. | 33/501.45 |
| 5,476,510 | * 12/1995 | Eberhardt et al. | 623/2 |
| 5,489,296 | * 2/1996 | Love et al. | 623/2 |
| 5,496,346 | * 3/1996 | Horzewski et al. | 606/194 |
| 5,752,522 | * 5/1998 | Murphy | 128/774 |
| 5,885,228 | * 3/1999 | Rosenman et al. | 600/587 |
| 6,042,554 | * 3/2000 | Rosenman et al. | 600/587 |

FOREIGN PATENT DOCUMENTS

| | | |
|---|---|---|
| 2681775 | 4/1993 | (FR) . |
| WO 81/02098 | 8/1981 | (WO) . |
| WO 87/05489 | 9/1987 | (WO) . |

* cited by examiner

Primary Examiner—Max Hindenburg
(74) Attorney, Agent, or Firm—Hoekendijk & Lynch, LLP (57) ABSTRACT

A valve sizer having a movable element mounted to the distal end of a shaft. A valve sizing portion includes the movable element so that the valve sizing portion may be adjusted to correspond to a number of different available replacement valve sizes. An indicator mounted to the proximal end of the shaft indicates the valve size corresponding to the outer dimension of the valve sizing portion.

15 Claims, 10 Drawing Sheets

VALVE SIZER

CROSS-REFERENCE TO RELATED APPLICATIONS

This application is a continuation of U.S. patent application Ser. No. 09/273,955 filed Mar. 22, 1989, now U.S. Pat. No. 6,042,554 which is a divisional of U.S. patent application Ser. No. 08/646,850, filed May 8, 1996, now U.S. Pat. No. 5,885,228.

FIELD OF THE INVENTION

The present invention is directed to methods and apparatus for determining the appropriate replacement valve size when replacing a patient's cardiac valve.

BACKGROUND OF THE INVENTION

Replacement of a diseased or malfunctioning cardiac valve requires accurate sizing of the valve annulus. After the diseased or malfunctioning cardiac valve has been removed, the surgeon measures the patient's valve annulus to determine the appropriate replacement valve size.

A conventional system for measuring a patient's valve annulus includes a number of varying size discs which can be attached to a rod. Each of the discs has a size which corresponds to an available valve size. The surgeon attaches one of the discs to the rod, inserts the disc into the patient's valve annulus and checks the fit of the disc within the valve annulus. If the surgeon is not satisfied with the fit, the surgeon removes the disc from the rod, attaches another disc to the rod and inserts the new disc into the valve annulus. This procedure is repeated until the surgeon is satisfied that the appropriate valve size has been identified.

A problem with the known method and apparatus for sizing a patient's valve annulus is the time required to try a number of discs. For each valve size the surgeon tries, the surgeon must remove one of the discs and attach another one. This procedure increases the overall surgery time which increases the risk to the patient and also increases the cost of the procedure.

Thus, it is a specific object of the present invention to reduce the amount of time required to size a patient's valve annulus by providing a device which can identify a number of different appropriate valve sizes without requiring withdrawal of the device from the patient.

SUMMARY OF THE INVENTION

The present invention solves the problems with the prior art by providing a valve sizer which is only introduced into the patient once and can identify a number of appropriate replacement valve sizes. The valve sizer includes an elongate shaft having a proximal end and a distal end with a movable element coupled to the distal end of the shaft. A valve sizing portion has an outer dimension which is at least partially defined by the movable element. A valve size indicator is provided at the proximal end of the shaft. An actuator is also provided at the proximal end for moving the movable element so that the valve sizing portion corresponds to the various valve sizes.

In a preferred embodiment, the movable element includes a plurality of arms having outer surfaces generally forming a circular shape. A rod extends through the shaft and is operatively coupled to the actuator. The rod is rotatable relative to the shaft so that rotation of the rod moves the movable element. A disc is attached to the rod. The disc has a plurality of slots which receive pins attached to the plurality of arms. Camming surfaces are coupled to the shaft and configured to engage and cam the plurality of arms when the actuator is actuated to move the movable element.

In another preferred embodiment, the valve sizer includes a ring mounted to an elongate shaft. An actuator is mounted to the proximal end of the shaft and is operatively coupled to the ring for expanding and retracting the ring. The ring preferably includes a first part and a second part slidably coupled to the first part. The second part is slidably received in a recess in the first part. Two levers are connected to the ends of the first part. One of the levers is attached to the shaft and another lever is attached to a rod extending through the shaft so that rotation of the rod relative to the shaft expands and retracts the ring.

In yet another preferred embodiment, the valve sizer has a balloon mounted to a tube having a lumen therethrough. The balloon is coupled to the lumen so that the balloon may be inflated with a fluid passing through the lumen. The tube preferably includes a valve size indicator which indicates an outer dimension of the balloon when the balloon is inflated.

These and other features will become apparent with the following description of the preferred embodiments.

DESCRIPTION OF THE PREFERRED EMBODIMENTS

Figure 1:
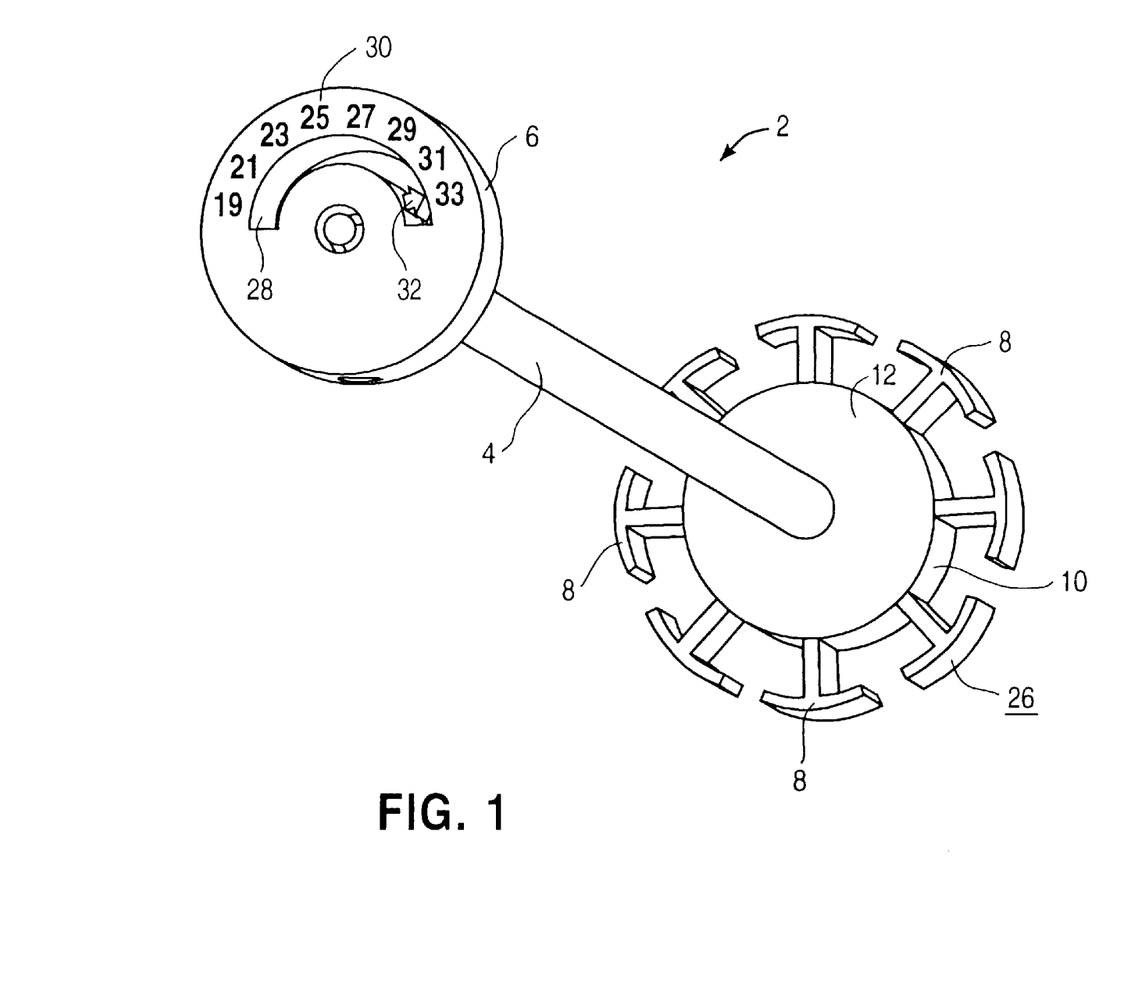
FIG. 1 is a perspective view of a first valve sizer having arms in an expanded position.
Figure 2:
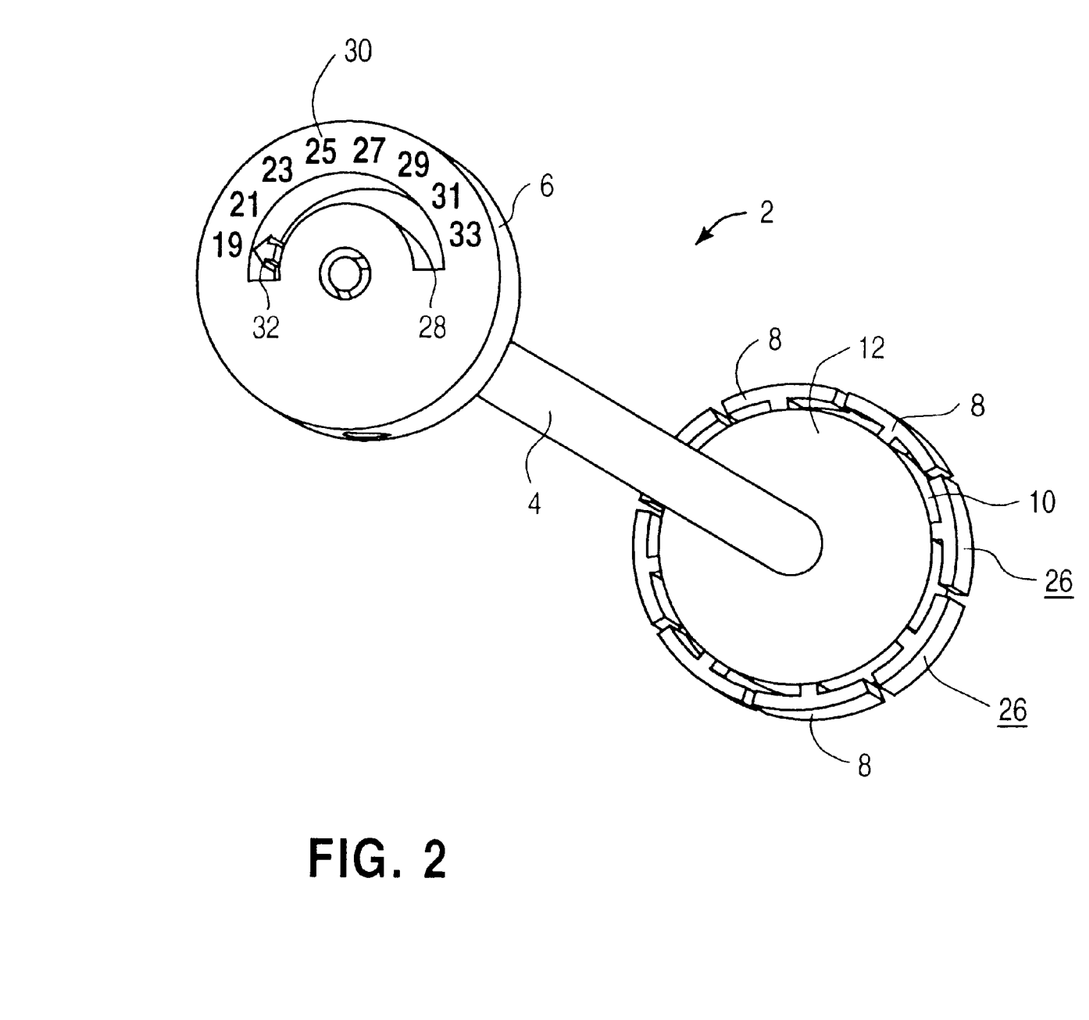
FIG. 2 shows the first valve sizer of FIG. 1 with the arms in a retracted position.

Referring to FIGS. 1 and 2, a first valve sizer 2 is shown. The valve sizer 2 has a tube 4 and an actuator 6 at the proximal end of the tube 4. A number of arms 8 extend radially outward from a spacer 10 which is coupled to the tube 4 as described below. FIG. 1 illustrates the arms 8 in an extended position and FIG. 2 illustrates the arms 8 in a retracted position. Rotation of the actuator 6 moves the arms 8 from the retracted position to the expanded position as will be described below.

Figure 3:
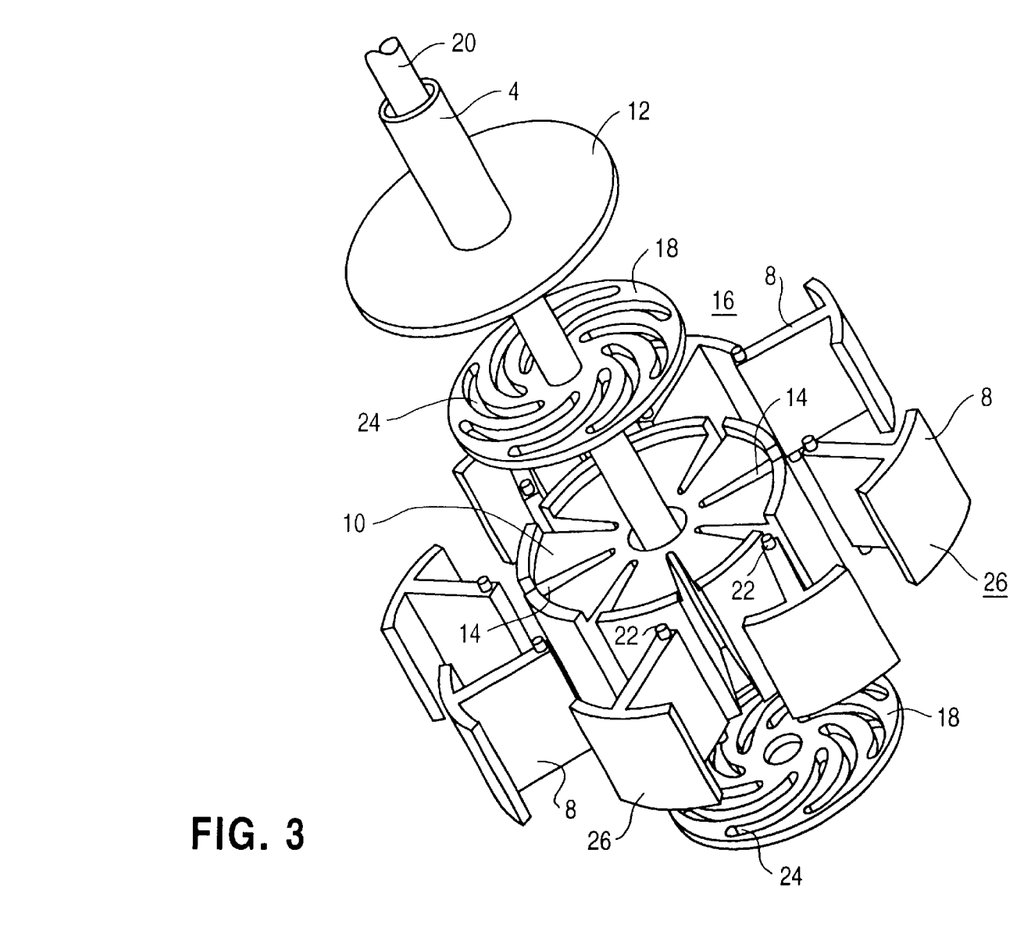
FIG. 3 is an exploded perspective view of the distal end of the first valve sizer.

Referring to FIG. 3, the distal end of the valve sizer 2 is shown. The spacer 10 is attached to the bottom of a disc 12 which is attached to the tube 4. The spacer 10 includes slots 14 which guide movement of the arms 8 between the retracted and extended positions. The spacer 10 includes two recesses 16, only one of which is shown, which receive slotted discs 18. The slotted discs 18 are mounted to a rod 20 which extends through the tube 4. As will be discussed below, the rod 20 and tube 4 are coupled to the actuator 6 so that rotation of the actuator 6 rotates the rod 20 and slotted discs 18 with respect to the tube 4. Thus, the rod 20 and slotted discs 18 form a unitary structure while the tube 4, disc 12 and spacer 10 form another unitary structure.

Figure 4:
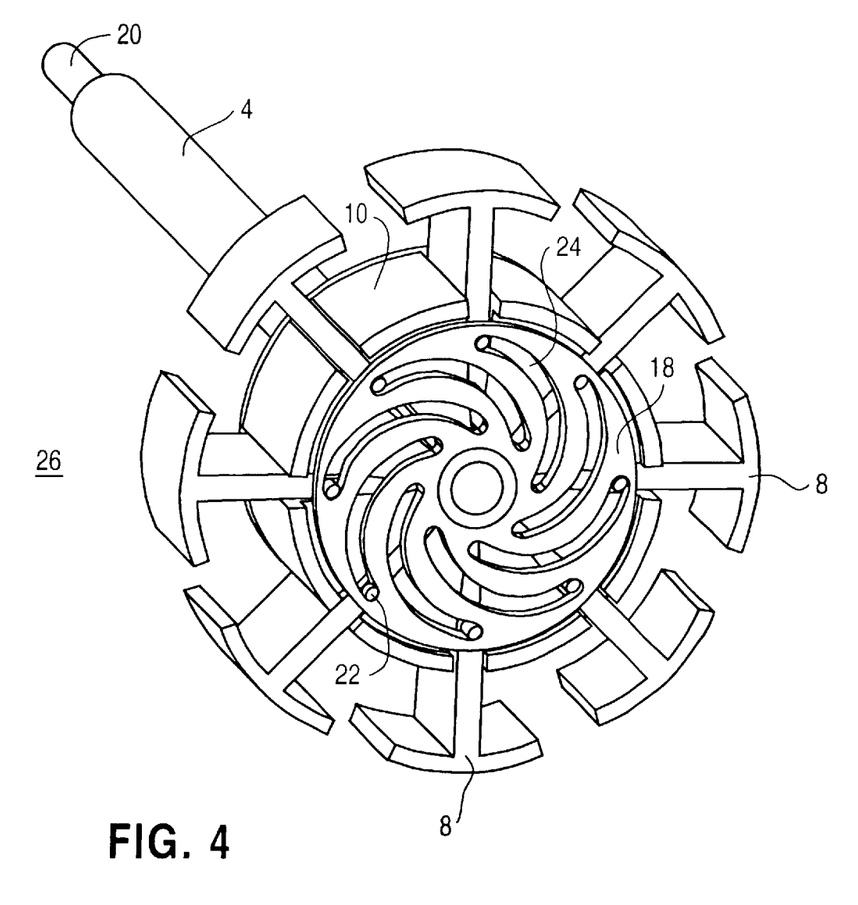
FIG. 4 is a bottom perspective view of the first valve sizer with the arms in the expanded position.

The arms 8 include pins 22 which are positioned in slots 24 of the slotted discs 18. Rotation of the rod 20 causes the pins 22 to slide in the slots 24 of the slotted discs 18 thereby moving the arms 8 in the slots 14 of the spacer 10 between the expanded and retracted positions. Referring to FIG. 4, a bottom view is shown with the arms 8 in the expanded position.

The arms 8 are preferably T-shaped with a curved outer surface 26 but may take any other shape. The outer surfaces 26 of the arms 8 generally form a circular peripheral shape when in the retracted and expanded positions. The outer surfaces 26 of the arms 8 define a valve sizing portion which engages the patient's valve annulus when sizing the replacement valve. The maximum outer dimension of the valve sizer 2 is preferably no more than 17 mm, more preferably no more than 18 mm, and most preferably no more than 19 mm, when in the retracted position. The outer surfaces 26 of opposing arms 8 preferably have a maximum outer dimension of at least 30 mm and more preferably at least 33 mm when in the expanded position. The preferred dimensions of the valve sizer 2 in the retracted position permits insertion of the valve sizer 2 between adjacent ribs in a patient when performing a minimally invasive valve procedure such as described in U.S. patent application No. 08/163,241 to Sterman et al., filed Dec. 6, 1993, which is incorporated herein by reference. Alternatively, the valve sizer 2 may be provided in two size ranges, preferably 17–27 mm and 23–33 mm.

Referring again to FIGS. 1 and 2, the actuator 6 includes a slot 28 with markings 30 indicating various valve sizes. A pointer 32 is coupled to the tube 4 and points to the marking 30 indicating the valve size corresponding to the outer dimension of the arms 8. The actuator 6 is coupled to the rod 20 so that rotation of the actuator 6 causes the pointer 32 to move along the slot 28. The markings 30 preferably indicate an outer diameter of 19 to 33 mm. Although it is preferred to use the rotating actuator 6 to move the arms 8, any other actuation mechanism may be used including a trigger, sliding lever, or scissors-type actuator 6.

A method of selecting an appropriate valve size is now described with reference to FIGS. 1–3. A method of replacing a patient's cardiac valve is described in U.S. patent application No. 08/163,241. The valve sizer 2 is preferably introduced into the patient between adjacent ribs in the patient without cutting or significantly deflecting the ribs. The valve sizer 2 is sized and configured so that it has a profile of no more than 20 mm, and more preferably no more than 19 mm, so that the valve sizer 2 may be introduced between adjacent ribs in the patient. The surgeon then positions the arms 8 in the valve annulus and rotates the actuator 6 until the arms 8 contact the valve annulus. The surgeon then reads the appropriate valve size with the pointer 32 and markings 30. The actuator 6 is then rotated again so that the arms 8 are in the retracted position of FIG. 2 for removing the valve sizer 2 from the patient.

Figure 5:
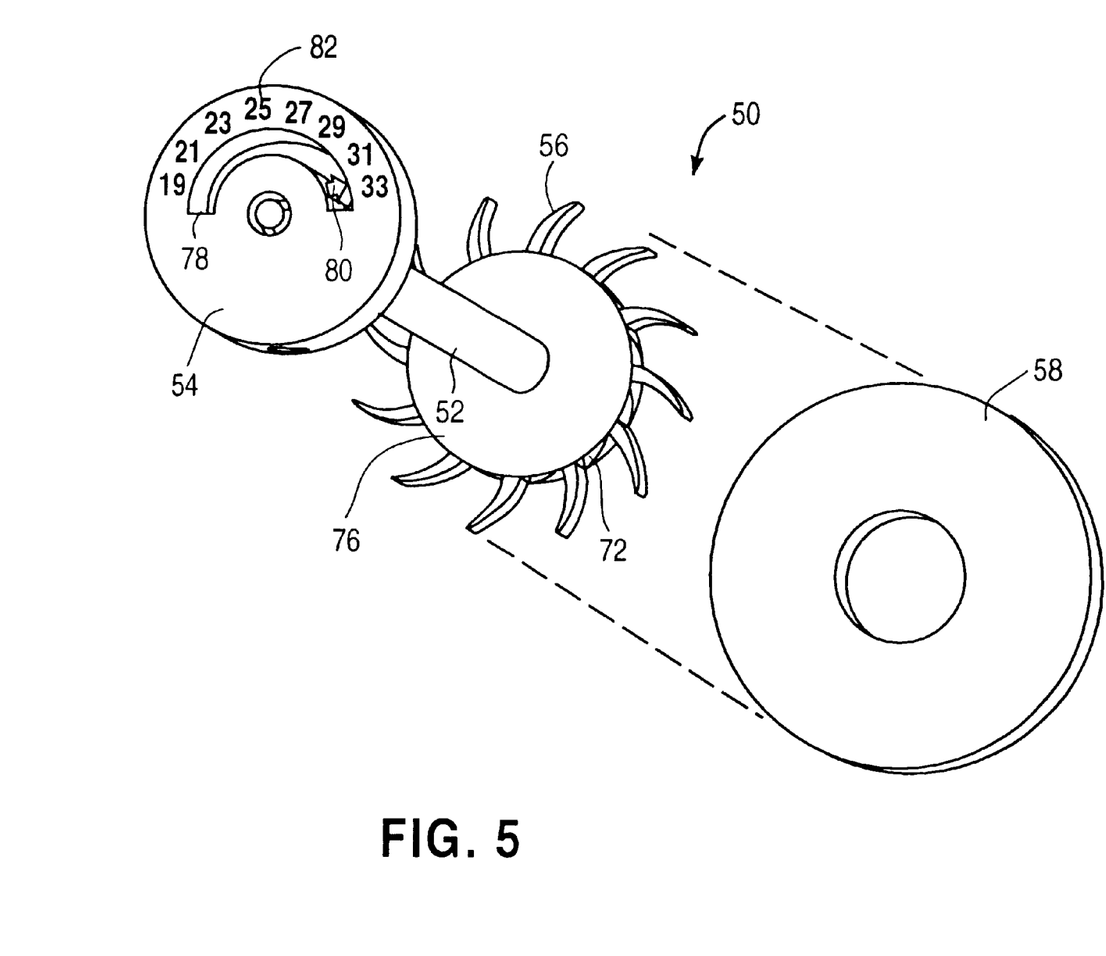
FIG. 5 is a perspective view of a second valve sizer having arms in an expanded position with a sheath exploded from the assembly for clarity.
Figure 6:
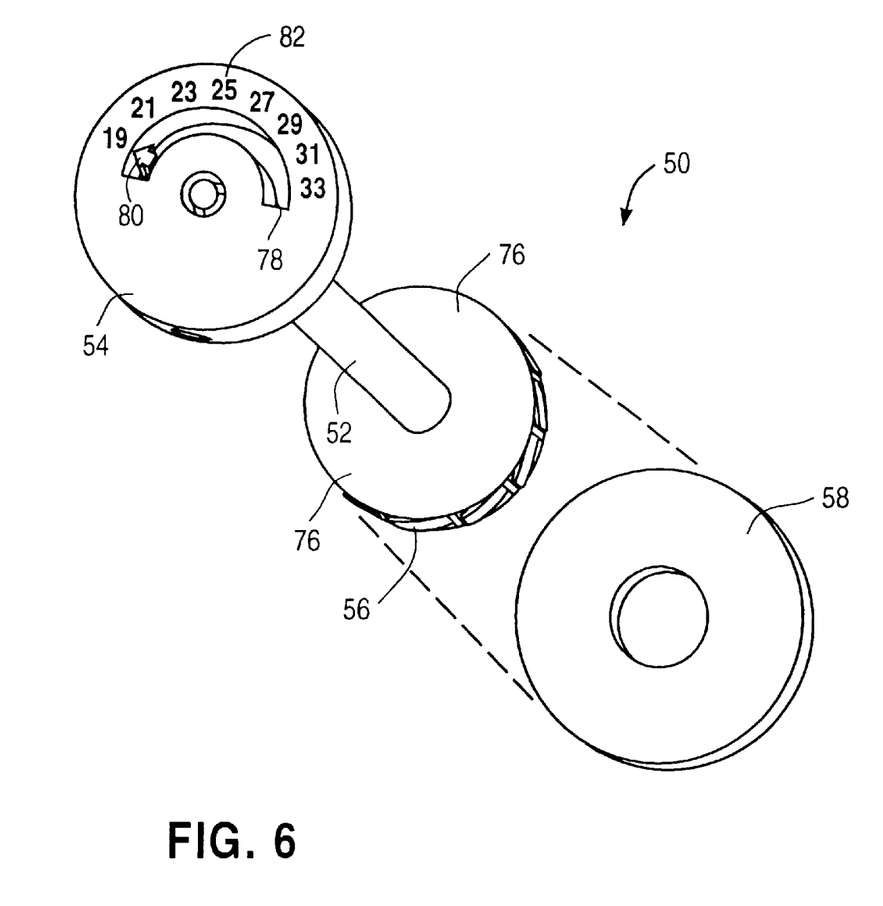
FIG. 6 shows the second valve sizer of FIG. 5 with the arms in a retracted position and the sheath exploded from the assembly for clarity.

Referring to FIGS. 5 and 6, a second preferred valve sizer 50 is shown. The valve sizer 50 includes a tube 52 having an actuator 54 at the proximal end. A number of arms 56 are movable from the retracted position shown of FIG. 1 to the expanded position shown in FIG. 2. A flexible sheath 58 is positioned around the arms 56 but is shown separated from the device for clarity. The sheath 58 is preferably made of silicone, however, any other suitable material may be used.

Figure 7:
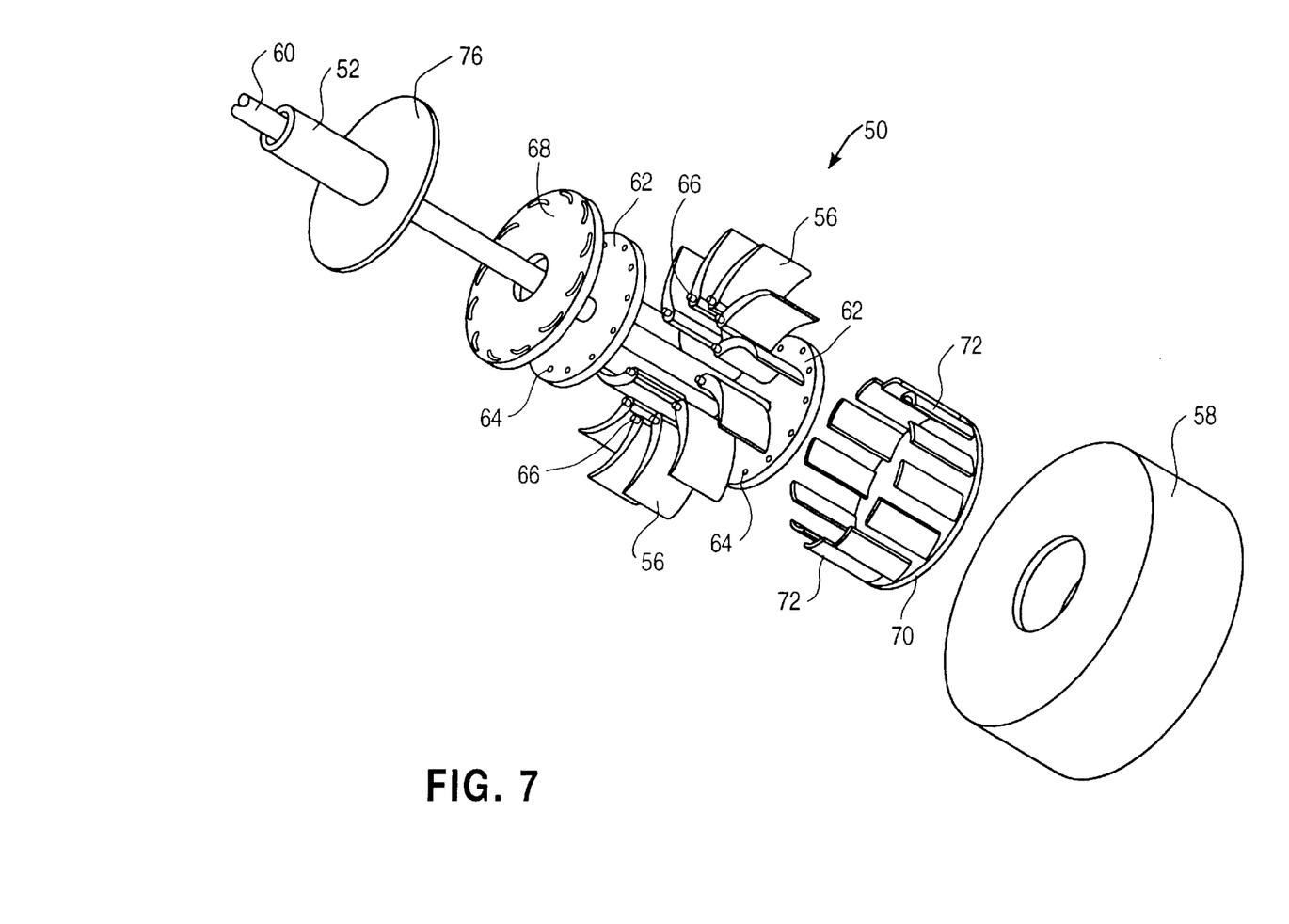
FIG. 7 is an exploded perspective view of the distal end of the second valve sizer.

An exploded view of the distal end of the second preferred valve sizer 50 is shown in FIG. 7. A shaft 60 extends through the tube 52 and is connected to the actuator 54 as will be described below. Two discs 62 having holes 64 therein are mounted to the shaft 60. The arms 56 have pins 66 which engage the holes 64 in the discs 62 so that the arms 56 are free to rotate relative to the discs 62. The arms 56 are preferably curved but may take any other shape. The outer dimensions of the valve sizer 50 in the expanded and retracted positions are preferably the same as the first valve sizer 2 described above. The tube 52 preferably has a length sufficient to reach the patient's valve annulus when the actuator 54 is positioned outside the patient's chest.

Top and bottom plates 68, 70 are attached a sealing plate 76 which is attached to the tube 52. The bottom plate 70 has a number of camming elements 72 which engage the arms 56 for moving the arms 56 from the retracted to expanded position as described below. The top plate 68 has openings 74 which receive the camming elements 72. Thus, the top and bottom plates 68, 70, sealing plate 76 and tube 52 form a unitary structure. Although it is preferred to provide the top plate 68, the top plate 68 may be omitted and the camming elements 72 may be attached directly to the sealing plate 76.

The camming elements 72 are positioned and configured to engage and deflect the arms 56 outward when the shaft 60 is rotated. The camming elements 72 are curved members but may take any other shape which cooperates with the arms 56 to cam the arms 56 outward when the shaft 60 is rotated with respect to the tube 52. The valve sizer 50 may include a locking mechanism (not shown), such as a ratchet and pawl, for locking the valve sizer 50. Alternatively, the actuator 54 may be designed with frictional resistance to turning which effectively locks the arms 56.

Referring again to FIGS. 5 and 6, the actuator 54 has a slot 78 which receives a pointer 80. The pointer 80 is coupled to the tube 52 so that the pointer 80 moves along the slot 78 when the actuator 54 is rotated. The actuator 54 includes markings 82 which indicate the valve size corresponding to the size defined by the outer dimension of the arms 56 and sheath 58. The markings 82 preferably indicate an outer diameter of between 19 and 33 mm. Although it is preferred to use the rotating actuator 54, any other actuation mechanism may be used. The method of using the second valve sizer 50 is the same as the first valve sizer 2 and a description of the method of use is omitted here.

Figure 8:
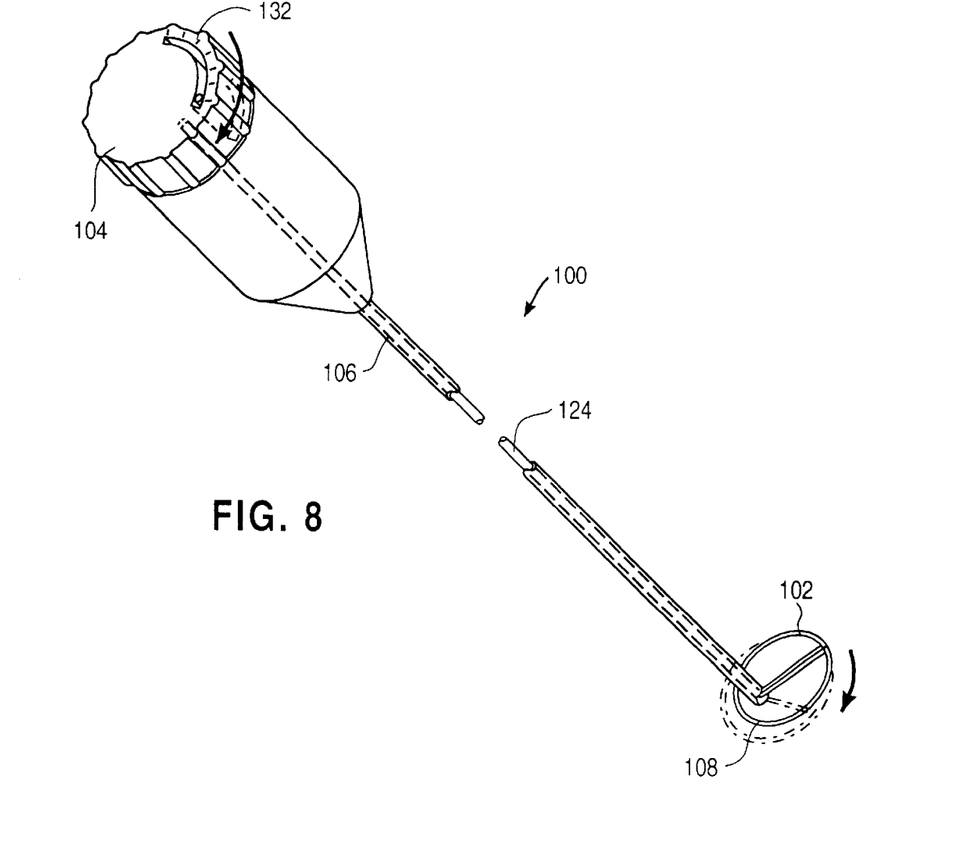
FIG. 8 is a perspective view of a third valve sizer having an expandable ring.
Figure 9:
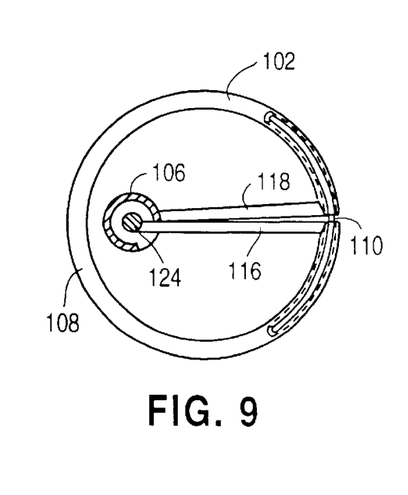
FIG. 9 shows the ring of the third valve sizer in a retracted position.
Figure 10:
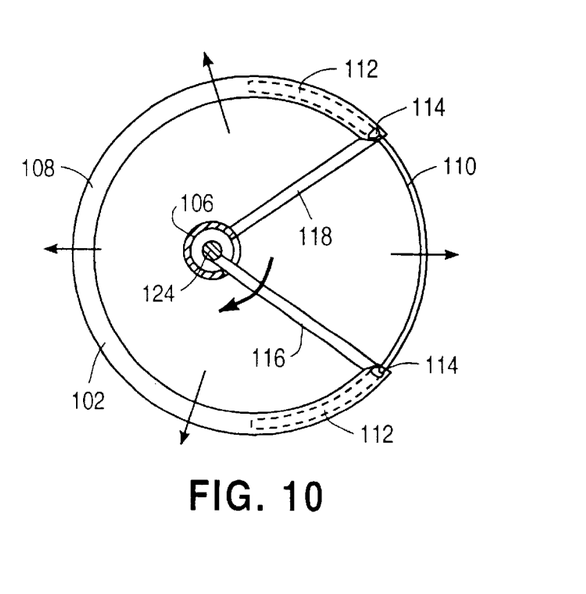
FIG. 10 shows the ring of the third valve sizer in an expanded position.

Referring to FIGS. 8–10, a third valve sizer 100 is shown. The third valve sizer 100 has a ring 102 which is movable between the retracted position of FIG. 9 to the expanded position of FIG. 10. An actuator 104 is mounted to the proximal end of a tube 106 and is used to move the ring 102 between the retracted and expanded positions as will be described in greater detail below.

The ring 102 includes a first part 108 and a second part 110 slidably coupled to the first part 108. Both the first and second parts 108. 110 are flexible so that they can assume the expanded and retracted positions of FIGS. 9 and 10. The first part 108 has recesses 112 which are sized to slidably receive the second part 110. The second part 110 includes stops 114 which prevent the first and second parts 108, 110 from becoming detached. First and second levers 116, 118 are attached to first and second ends 120, 122 of the first part 108, respectively. The first lever 116 is attached to a shaft 124 and the second lever 118 is attached to the tube 106 so that rotation of the shaft 124 relative to the tube 106 moves the first and second levers 116, 118 with respect to one another.

The actuator 104 has an arcuate slot 128 therein which receives a pin 130 attached to the tube 106. The actuator 104 is attached to the shaft 124 so that rotation of the actuator 104 moves the first lever 116 with respect to the second lever 118. The actuator 104 also preferably includes size indicators 132 which indicate the valve size corresponding to the size of the ring 102. The ring 102 preferably has the same dimensions as the arms 56 of the first valve sizer when in the expanded and retracted positions.

Use of the third valve sizer 100 is now described. The valve sizer 100 is introduced into the patient with the ring 102 in the retracted position of FIG. 9. The surgeon positions the ring 102 within the valve annulus and rotates the actuator 104 until the ring 102 engages the valve annulus. The surgeon then reads the indicators 132 to determine the appropriate valve size. The actuator 104 is rotated so that the ring 102 assumes the retracted position and the valve sizer 100 is removed from the patient. Although it is preferred to provide the first and second levers 116, 118 for the expandable ring 102, any other mechanism may be used including a ring 102 having teeth which engage a rotatable gear. Alternatively, the ring 102 may be a flexible ring which simply extends from the distal end of the shaft with the ring being expanded and retracted by simply lengthening or shortening the flexible ring Furthermore, although the ring 102 is preferably relatively flat, the ring 102 may be somewhat thick to form a cylinder without departing from the scope of the invention.

Figure 11:
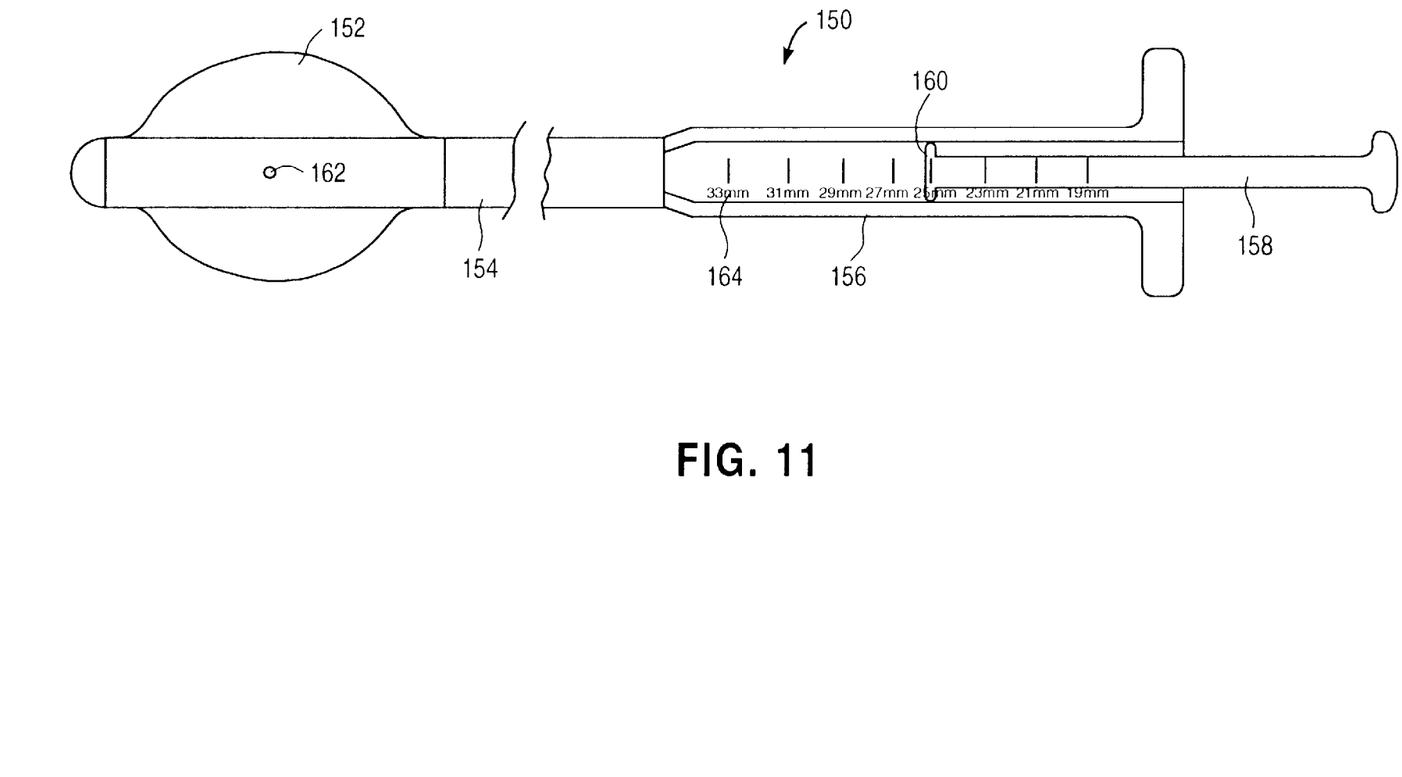
FIG. 11 shows a fourth valve sizer having an inflatable balloon.

Referring to FIG. 11, a fourth preferred valve sizer 150 is shown. The valve sizer 150 includes a balloon 152 mounted to the distal end of a rigid tube 154. A cylinder 156 is attached to the proximal end of the tube 154 and a plunger 158 having a piston 160 is slidable within the cylinder 156. The tube 154 has a hole 162 through which the inflation fluid passes for inflating the balloon 152. The balloon 152 may be made of any conventional elastomeric material and is preferably made of polyurethane or a thermoplastic elastomer.

The cylinder 156 is calibrated so that a given volume of fluid or gas injected into the balloon 152 expands the balloon 152 to a known size. The cylinder 156 preferably includes indicators 164 which indicate the valve size corresponding to the diameter of the balloon 152. The balloon 152 is inflated and deflated by manipulating the plunger 158. The balloon 152 preferably has a maximum outer dimension of no more than 17 mm, and more preferably no more than 19 mm, and expands to a maximum outer dimension of at least 30 mm and more preferably at least 33 mm. Although the balloon 152 is shown as being somewhat elongate the balloon 152 may also take any other shape such as a torus, sphere or any other suitable shape. Furthermore, although it is preferred that the balloon 152 expand around the entire periphery of the tube the balloon 152 may be configured to expand from a side of the tube 154 rather than all around the tube 154. Although tube 154 is preferably rigid, the tube 154 may be malleable to allow the tube 154 to conform to a desired shape A method of using the fourth valve sizer 150 is now described. The balloon 152 is inserted into the patient's valve annulus in the deflated condition and the surgeon depresses the plunger 158 until the balloon 152 engages the valve annulus. The surgeon then reads the indicators 164 to determine the appropriate valve size. The balloon 152 is then deflated and the valve sizer 150 is removed from the patient.

Figures 12, 13, 14:
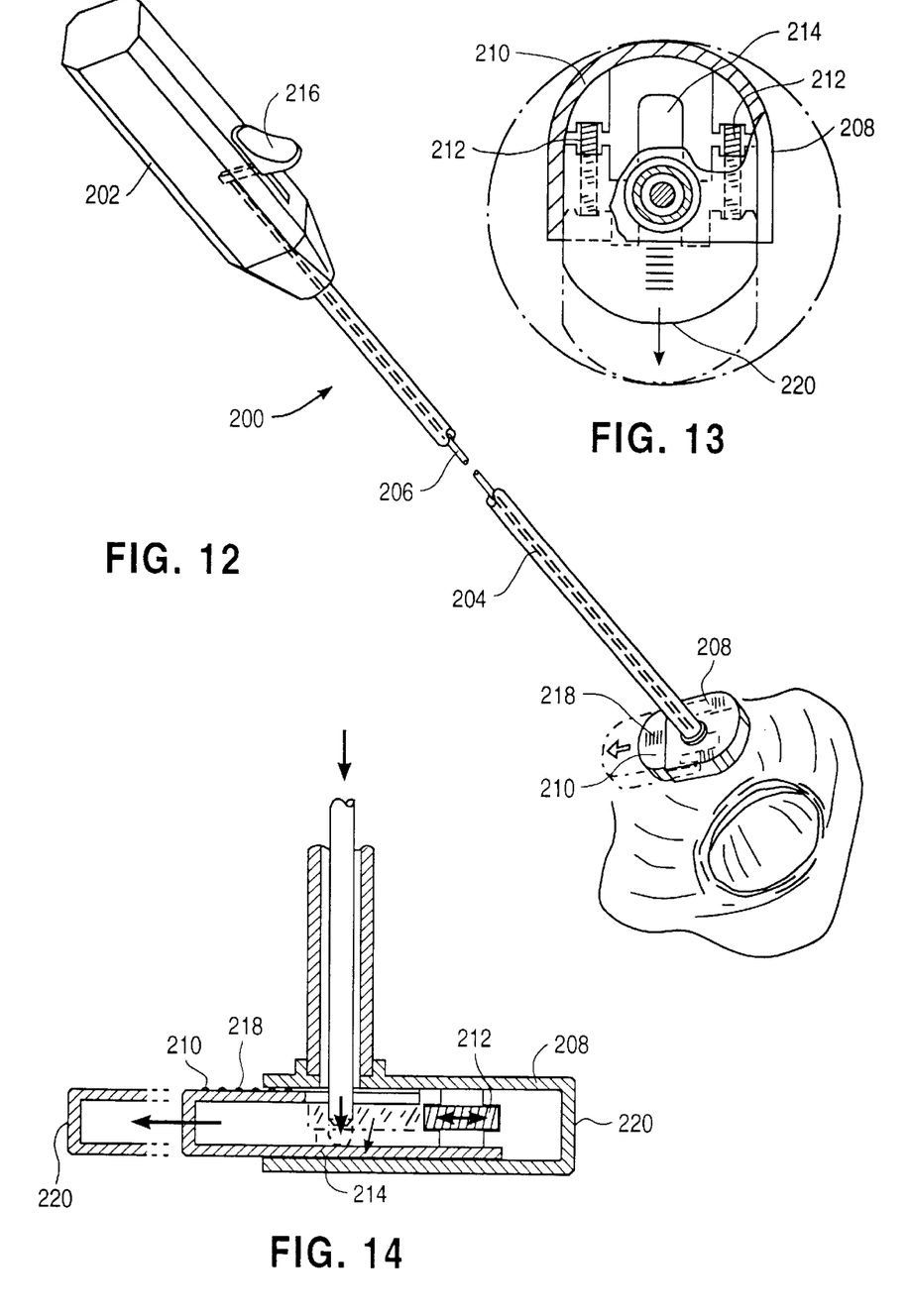
FIG. 12 is a perspective view of a fifth valve sizer.
FIG. 13 is a partial cut-away of the distal end of the fifth valve sizer.
FIG. 14 is a cross-sectional view of the distal end of the fifth valve sizer.

Referring to FIGS. 12–14, a fifth valve sizer 200 is shown. The fifth valve sizer 200 has a handle 202 from which extends a tube 204 and a shaft 206. A first element 208 is attached to the tube 204. A second element 210 is linearly slidable with respect to the first element 208 from the retracted solid-line position of FIG. 13 to the expanded, dotted-line position of FIG. 13. A pair of springs 212 bias the first and second elements 208, 210 toward the expanded position.

Referring to FIGS. 13 and 14, the tube 204 is attached to the first element 208 at a flange. The shaft 206 extends through the first element 208 toward a deflectable tongue 214 attached to the second element 210. The first and second elements 208, 210 are locked to one another by moving the shaft 206 downward into contact with first element 208 by actuating thumb switch 216 (FIG. 12) which is coupled to the shaft 206. The tongue 214 is deflected downwardly by the shaft 206 into frictional engagement with the first element 208 to lock the first and second elements 208, 210 together. The second element 210 preferably includes valve size indications 218 which indicate the valve size corresponding to the size between outer edges 220 of the first and second elements 208, 210. The fifth valve sizer 200 preferably has the same dimensions as the first valve sizer 2 when in the expanded and retracted positions. Although it is preferred to use the springs 212 and the deflectable tongue 214 to move and lock the first and second elements 208, 210 together, it is within the scope of the invention to provide any other moving and locking mechanism. For example, the fifth valve sizer 200 may include a rotatable shaft having a gear which engages a rack in the second element 210 for moving the second element 210 with respect to the first element 208. A proximal size indicator could be used with the gear and rack configuration.

Use of the fifth valve sizer 200 is now described. The valve sizer 200 is introduced into the patient's valve annulus with the first and second elements 208, 210 in the retracted position. The surgeon then manipulates the thumb switch 216 so that the shaft 206 moves proximally and releases the tongue 214. The first and second elements 208, 210 are then biased outwardly by the springs 212 until they contact the valve annulus. The surgeon then manipulates the thumb switch 216 again to lock the first and second elements 208, 210 together. The surgeon then removes the valve sizer 200 and reads the valve sizer indications 218 to determine the appropriate valve size.

The above description merely describes the preferred embodiments and it is understood that variations of the preferred embodiment are within the scope of the invention which is defined by the claims. For example, although the preferred valve sizers are attached to shafts which do not articulate it is within the scope of the invention to provide articulating or malleable shafts so that the distal ends may be pivoted. Furthermore, although it is preferred to use the valve sizers when performing a minimally invasive valve replacement procedure, the valve sizer may also be used in a conventional open-chest procedure.

What is claimed is:

1. A valve sizer for determining an appropriate replacement valve size when performing a valve replacement procedure, comprising:
   a shaft having a proximal end and a distal end;
   a movable element coupled to the distal end of the shaft, the movable element being movable between a first position and a second position;
   a valve sizing portion having an outer dimension, the valve sizing portion being at least partially defined by the movable element;
   an indicator at the proximal end of the shaft, the indicator indicating a replacement valve size corresponding to the outer dimension of the valve sizing portion; and
   an actuator at the proximal end of the elongate shaft, the actuator being operatively coupled to the movable element for moving the movable element between the first and second positions.

2. The valve sizer of claim 1, wherein:
   the movable element includes a plurality of arms, the plurality of arms having outer surfaces generally forming a generally circular shape in a plane perpendicular to a longitudinal axis defined by the shaft, the plurality of arms being movable between the first and second positions.

3. The valve sizer of claim 1, wherein:
   the plurality of arms move in a plane substantially perpendicular to a longitudinal axis defined by the shaft.

4. The valve sizer of claim 1, further comprising:
   a rod extending through at least a portion of the shaft, the rod being operatively coupled to the actuator.

5. The valve sizer of claim 4, wherein:
   the rod is rotatable relative to the shaft, the rod being coupled to the actuator so that rotation of the rod relative to the shaft moves the movable element between the first and second positions.

6. The valve sizer of claim 4, further comprising:
   a disc attached to the rod;
   the movable element including a plurality of arms;
   the disc having a plurality of slots which receive pins attached to the plurality of arms.

7. The valve sizer of claim 1, further comprising:
   a plurality of camming surfaces coupled to the shaft, the plurality of camming surfaces being configured to engage and cam the plurality of arms when the actuator is actuated to move the movable element from the first position to the second position.

8. The valve sizer of claim 1, wherein:
   the outer dimension is no more than 21 mm when the movable element is in the first position.

9. The valve sizer of claim 8, wherein:
   the outer dimension is no more than 19 mm when the movable element is in the first position.

10. The valve sizer of claim 8, wherein:
    the outer dimension is at least 31 mm when the movable element is in the second position.

11. The valve sizer of claim 8, wherein:
    the outer dimension is at least 33 mm when the movable element is in the second position.

12. A valve sizer for measuring a patient's valve annulus, comprising:
    a shaft having a distal end and a proximal end;
    a ring mounted to the distal end of the shaft, the ring being movable from a first position to a second position, the first position having a smaller diameter than the second position; and
    an actuator mounted to the proximal end of the shaft, the actuator being operatively coupled to the ring for moving the ring from the first position to the second position.

13. The valve sizer of claim 12, wherein:
    the ring includes a first part and a second part slidably coupled to the first part.

14. The valve sizer of claim 12, wherein:
    the second part is slidably received in a recess in the first part, the first part having first and second ends.

15. The valve sizer of claim 14, further comprising:
    a first lever coupled to the first end of the first part;
    a second lever coupled to the second end of the first part, the second lever being rotatable relative to the first lever;
    the actuator being operatively coupled to at least one of the first and second levers for rotating the first lever with respect to the second lever.

* * * * *